(12) United States Patent
Yako et al.

(10) Patent No.: US 7,319,156 B2
(45) Date of Patent: Jan. 15, 2008

(54) PROCESS FOR PRODUCING OLEFIN OXIDE

(75) Inventors: Makoto Yako, Ibaraki (JP); Michio Yamamoto, Otsu (JP)

(73) Assignee: Sumitomo Chemical Company, Limited, Osaka (JP)

( * ) Notice: Subject to any disclaimer, the term of this patent is extended or adjusted under 35 U.S.C. 154(b) by 401 days.

(21) Appl. No.: 10/804,231

(22) Filed: Mar. 19, 2004

(65) Prior Publication Data

US 2005/0113587 A1  May 26, 2005

(30) Foreign Application Priority Data

Mar. 25, 2003  (JP) .............................. 2003-082388

(51) Int. Cl.
*C07D 301/10* (2006.01)

(52) U.S. Cl. ...................... 549/534; 549/536; 502/243; 502/303; 502/347; 502/348

(58) Field of Classification Search ................ 549/534, 549/536; 502/303, 347, 243, 348
See application file for complete search history.

(56) References Cited

U.S. PATENT DOCUMENTS

| 5,387,751 A | * | 2/1995 | Hayden et al. ............. 549/534 |
| 5,618,954 A | | 4/1997 | Boeck et al. |
| 5,625,084 A | | 4/1997 | Pitchai et al. |
| 5,801,259 A | * | 9/1998 | Kowaleski .................. 549/536 |
| 5,856,534 A | * | 1/1999 | Cooker et al. .............. 549/534 |
| 5,905,161 A | * | 5/1999 | Boeck et al. ................ 549/534 |
| 6,031,116 A | | 2/2000 | Bowman et al. |
| 6,392,066 B1 | * | 5/2002 | Mul et al. .................... 549/534 |
| 6,498,122 B2 | * | 12/2002 | Nakashiro ................... 502/347 |

FOREIGN PATENT DOCUMENTS

| EP | 0 318 815 A1 | 6/1989 |
| EP | 0 532 325 A1 | 3/1993 |
| GB | 500382 | 2/1939 |
| GB | 517333 | 1/1940 |
| GB | 1 368 922 | 10/1974 |
| JP | 1-231942 A1 | 9/1989 |
| JP | 2002-510306 A | 4/2002 |
| WO | WO 98/58921 A1 | 12/1998 |

OTHER PUBLICATIONS

Monnier, Applied Catalysis A: General 221 (2001) pp. 73-91.*
Lu, Guanzhong et al., 1999, "Epoxidation of propylene by air over modified silver catalyst", Catalysis Letters, vol. 58, No. 1, pp. 67-70. XP000825457.
Fessehaye W. Zemichael et al., "Propene epoxidation over K-promoted Ag/CaCO₃ catalysts: the effect of metal particle size", *Catalysis Letters*, vol. 80, No. 3-4, Jun. 2002, pp. 93-98.

* cited by examiner

*Primary Examiner*—Thomas McKenzie
*Assistant Examiner*—Raymond Covington
(74) *Attorney, Agent, or Firm*—Foley & Lardner LLP

(57) ABSTRACT

There is disclosed a process for producing an olefin oxide, which is characterized by reacting an olefin with oxygen in the presence of a silver catalyst and 0.2 mole or more of water per mol of the olefin.

8 Claims, No Drawings

PROCESS FOR PRODUCING OLEFIN OXIDE

BACKGROUND OF THE INVENTION

The present invention relates to a process for producing olefin oxide including propylene oxide, which is an important intermediate chemicals for the production of synthetic reagent, synthetic resin, or rubber.

For production method of olefin oxide, a method of reacting olefin with oxygen in the presence of silver catalyst is known (for example, JP-A-1-231942, which corresponds to U.S. Pat. No. 4,845,253, and JP-T 2002-510306, which corresponds to WO98/58921). The productivity of olefin oxide (epoxide) is not always satisfactory.

According to the present invention, olefin oxide can be readily produced by reacting an olefin with oxygen in the presence of a silver catalyst and 0.2 mol or more of water per mol of the olefin.

The silver catalyst that may be used in the present process is a silver catalyst containing silver or a silver compound or a mixture thereof, and the silver catalyst usually contains silver 1% by weight or more. The upper limit of the silver content is not particularly limited, and the silver catalyst containing silver less than 70% by weight may be used.

The silver metal may be a silver metal that is obtained by reducing a silver compound.

Examples of the silver catalyst include, for example, a silver-containing composition obtained by contacting silver metal or a silver compound or a mixture thereof with (A) at least one selected from the group consisting of an inorganic solid oxide, and a metal carbonate, and optionally (B) at least one selected from the group consisting of an acid and a nitrogen-containing compound; and calcined compositions thereof.

Examples of the silver catalyst include, for example, a silver-containing composition obtained by contacting a silver compound with 1) an inorganic solid oxide, and a metal carbonate, or
2) an inorganic solid oxide, a nitrogen-containing compound, and a reducing agent, or
3) a metal carbonate, and an acid, or
4) a metal carbonate, and a nitrogen-containing compound or
5) a metal carbonate, an acid and a nitrogen-containing compound; and a calcined composition of any one of 1) to 5) above.

Preferred are:

i) the silver-containing composition obtained by contacting a silver compound with a reducing agent in the presence of a metal carbonate, ii) the silver-containing composition obtained by contacting a) silver metal or a silver compound or a mixture thereof, with
b) an inorganic solid oxide,
c) an acid, and
d) a nitrogen-containing compound; and iii) a silver-containing composition obtained by contacting a) silver metal or a silver compound or a mixture thereof with
b) a metal carbonate,
c) an acid, and
d) a nitrogen-containing compound, and iv) a calcined silver-containing composition obtained by calcining the composition of i), ii) or iii) above.

Examples of the silver compound include, for example, silver oxide, silver carbonate, silver nitrate, silver sulfate, silver cyanide, silver halide (e.g. silver chloride, silver bromide, and silver iodide), silver carboxylate (e.g. silver acetate, silver benzoate, silver citrate, or silver lactate), and silver actylacetonate.

Examples of the reducing agent that may be used to reduce the silver compound include, for example, a reducing gas such as hydrogen, alcohols such as methanol, ethanol, propanol, butanol, ethyleneglycol, propyleneglycol, glycerine, aminoethanol, or dimethylaminoethanol, saccharides such as glucose, fructose, or galactose, aldehyde compounds such as formaldehyde, acetaldehyde, propylaldehyde, butyraldehyde, benzaldehyde, hydrazine compounds such as hydrazine, methylhydrazine, ethylhydrazine, propylhydrazine, butylhydrazine, or phenylhydrazine, metal hydrides such as lithium hydride, sodium hydride, potassium hydride, calcium hydride, or magnesium hydride, borohydride compounds such as boran, sodium borohydride, potassium borohydride, or dimethylaminoboran, and phosphites such as sodium hydrogen phosphite, or potassium hydrogen phosphite.

The reduction of the silver compound is typically conducted by reacting the silver compound with 0.1 mol to 20 moles of the reducing agent, usually at −30° C. to 300° C., preferably, 0° C. to 200° C.

Examples of the inorganic solid oxide include, for example, a) silicon oxides, or b) alumina, calcia (calcium oxide), magnesia, titania or zirconia, or complex metal oxides thereof (e.g. complex metal oxides comprising any two or more of the oxides of Si, Al, Ca, Mg, Ti, or Zr).

Examples of the silicon oxides typically include, silica gel(silicon dioxide) and silicates.

Examples of the silicates include, for example, i) water-soluble silicate such as sodium metasilicate or potassium metasilicate, ii) zeolite, which are typically crystalline silicates, having isomorphous framework structures such as zeolite β, ZSM-5, ZSM-11, ZSM-12, ZSM-48 or MCM-22, and iii) mesoporous silicates having mesopores with diameters of 2 nm to 50 nm, such as MCM-41, or MCM-48.

Examples of the silicates of ii) and iii) also include, for example, metallosilicates having incorporated Ti, Zr, Ga, Fe, B, V, Nb, Cr, Mo, Mn, Co, or Sn within their framework structures. The silicates of ii) and iii) may also be referred to as water-insoluble silicates.

Preferred silicon oxides that may be used for preparing the silver catalyst composition are silica gel and the water-insoluble silicates, more preferred are silica gel and the water-insoluble silicates of ii) and iii) consisting essentially of silicon dioxide.

The mesoporous silicates described above can be produced, for example, by hydrolyzing organic silicone compound such as tetraorthosilicate in the presence of a quaternary ammonium salt (U.S. Pat. No. 5,098,684, Zeolite, 18, 404-416 (1997)), a primary amine (Science, Vol. 267, 865) or a block co-polymer (Science, vol. 269, 1242) as a template, optionally followed by hydrothermal crystallization method, and removing the template by calcining at a temperature of 300 to 800° C. Alternatively, the silicate can be prepared in the presence of the silver compound.

Examples of the metal carbonate include, for example, an alkali metal carbonate such as sodium carbonate, potassium carbonate, rubidium carbonate, an alkaline earth metal carbonate such as magnesium carbonate, calcium carbonate, strontium carbonate, barium carbonate, and a rare earth metal carbonate such as scandium carbonate, cerium carbonate, or ytterbium carbonate. Preferred metal carbonates are the alkaline earth metal carbonate. An amount of the inorganic solid oxide or the metal carbonate that may be used is 0.1 to 120 parts by weight, preferably 0.1 to 30 parts by weight per part by weight of the silver contained in the silver metal or the silver compound or the mixture thereof.

Examples of the acid include, for example, an inorganic acid, and an organic acid. Preferred acid is the organic acid. Examples of the inorganic acid include, for example, hydrochloric acid, nitric acid, nitrous acid, sulfuric acid, and perchloric acid. Preferred inorganic acids are nitric acid and nitrous acid.

Examples of the organic acid include, for example, an aliphatic carboxylic acid such as oxalic acid, propionic acid, butanoic acid, citric acid, maleic acid, fumaric acid, or tartaric acid, and aromatic carboxylic acid such as benzoic acid, dicarboxybenzene, tricarboxybenzene, dicarboxynaphthalene and dicarboxyanthracene. Preferred organic acids are aliphatic carboxylic acid, and more preferred are oxalic acid, or citric acid. An amount of the acid that may be used is 0.1 mole to 10 moles per mol of the silver contained in the silver metal or the silver compound or the mixture thereof.

Examples of the nitrogen-containing compound include, for example, ammonia, and a nitrogen-containing organic compound such as an amine compound or an acid adduct salt thereof such as the amine carboxylate or the amine hydrochloride, an imine compound, amide compound, a nitrile compound, an organic nitroso compound, or an organic nitro compound, and a quaternary ammonium salt. Preferred are the amine compound and the acid adduct salt thereof such as the amine carboxylate (e.g. the amine acetate).

An amount of the nitrogen-containing compound that may be used is usually 0.1 mole to 20 moles per mol of the silver contained in the silver-metal or the silver compound or a mixture thereof.

Examples of the amine compound include, for example, a C1-20 aliphatic or aromatic amine compound such as methylamine, ethylamine, propylamine, n-butylamine, amylamine, hexylamine, heptylamine, octylamine, decylamine, dodecylamine, stearylamine, dimethylamine, diethylamine, dipropylamine, dibutylamine, trimethylamine, triethylamine, ethanolamine, diethanolamine, triethanolamine, diaminoethane, tetramethylenediamine, pentamethylenediamine, diethylenetriamine, aniline, benzylamine, phenylenediamine, and an amino acid such as glycin.

Examples of the imine compound include, for example, ethyleneimine, pyrrolidine, piperidine, and piperazine.

Examples of the amide compound include, for example, acetamide, and benzamide.

Examples of the nitrile compound include, for example, benzonitrile, and butyronitrile.

Examples of the nitro compound include, for example, nitrobenzene, and nitropyridine.

Examples of the nitroso compound include, for example, nitrosodimethylaniline, and nitrosonaphthol.

Examples of the quaternary ammonium salt include, for example, quaternary ammonium hydroxide such as tetramethylammonium, hydroxide, tetramethylammonium hydroxide, tetrapropylammonium hydroxide, and a quaternary ammonium halide such as tetramethylammonium chloride, or tetraethylammonium bromide.

The silver-containing composition of the present invention can be obtained by contacting silver metal or a silver compound or a mixture thereof with (A) at least one selected from the group consisting of an inorganic solid oxide, and a metal carbonate, and optionally (B) at least one selected from the group consisting of an acid and a nitrogen-containing compound, usually in a solvent such as water, methanol, ethanol, propanol, tetrahydrofuran, toluene, hexane or mixtures thereof, at 0 to 200° C. and concentrating the resulting. The silver-containing calcined composition can be obtained, for example, by calcining the silver-containing composition obtained as above at 200 to 700° C., preferably 300 to 700° C. in an air atmosphere. The silver-containing composition may be molded and then calcined, or the calcined composition may be molded thereafter.

The process of the invention may be conducted in a batch-wise or continuously, but is preferably conducted in a continuous reaction from an industrial viewpoint.

Catalytically effective amount of the silver catalyst described above is used in the present reaction. Typically, the amount of the silver catalyst that may be used is 0.00005 mol or more in terms of silver per mol of the olefin.

An amount of water that may be used is usually 0.2 mole or more per mol of the olefin, and upper limit thereof is no particularly limited as long as the amount of water does not adversely affect the process. The upper limit is typically 20 moles or less. Preferably the amount of water is 0.2 mole to 10 moles, more preferably 0.3 mole to 8 moles per mol of the olefin. The water may be supplied in a form of steam.

Examples of the olefin include, for example, a C2-6 olefin such as ethylene, propylene, 1-butene, 2-butene, isobutene, 1-pentene, and 1-hexene, and preferred is propylene. The olefin may be used as it is, or may be used as a mixture with an inert gas such as nitrogen, helium, or carbon dioxide. An amount of the inert gas that may be practically adapted is 50 moles or less per mol of the olefin.

The oxygen may be used alone or may be used as a gas mixture with the inert gas as described above. An amount of the oxygen that may be used varies according to the reaction mode, catalyst, reaction temperature, but is usually 0.01 mole to 100 moles, preferably 0.03 mole to 30 moles per mol of the olefin.

The reaction temperature is usually 100 to 400° C., and is preferably 120 to 300° C.

The process of the invention is conducted at a reaction temperature of slightly reduced pressure to slightly pressurized pressure and under such reaction pressure range in the co-presence of water, thereby olefin oxide is produced with good productivity. The reaction of the invention may be conducted typically at a pressure range of 0.01 to 1 MPa absolute, preferably 0.02 to 0.5 MPa absolute.

In the present reaction, the silver catalyst, water and olefin are mixed to bring them in contact with each other.

After the reaction, the reaction liquid or the reaction gas is collected and isolated by conventional separation method such as distillation.

Examples of the olefin oxide thus obtained include, for example, ethylene oxide, propylene oxide, butene oxide, and pentene oxide.

EXAMPLES

The present invention is explained by way of examples in more detail as follows, but it is not limited thereto.

Reference Example 1

4 g of crystalline silica having a framework MFI structure isomorphous to that of ZSM-5 and 40 g of ion-exchange water are added to a flask at 20-25° C. and under agitating 2.1 g of silver nitrate are added thereto and after having agitated at an inner temperature of 60° C. for 1 hour, the resulting was dried by evaporation to give a solid material. The obtained powder was molded by a tablet molding device, and the molded material was sieved out with 24-48 mesh-screen and the sieved material was charged into a calcining tube made of glass and calcined under an air flow of 100 mL/minute at 500° C. for 3 hours to give a silver catalyst.

Examples 1 to 3

2 mL of the silver catalyst obtained in the reference example 1 charged into a fixed-bed glass tube reactor having 10 mm inside diameter, at atmospheric pressure (corresponds to 0.1 MPa absolute) at a reaction temperature of 200° C., propylene was fed at 360 mL/Hr, air was fed at 360 mL/Hr, and water was supplied in such an amount as shown in table 1 and reacted. The results are shown in the following Table 1.

TABLE 1

|  | Example | | | |
| --- | --- | --- | --- | --- |
| Conditions | Ex. 1 | Ex. 2 | Ex. 3 | Comparative Ex. 1 |
| Water feed (mL/Hr) | 0.3 | 1 | 2 | 0 |
| Conv. of Propylene (%) | 1.4 | 3.4 | 3.8 | 0.7 |
| Propylene oxide (μmol/Hr) | 29 | 61 | 79 | 1 |

Comparative Example 1

In Example 1, the experiment was carried out in a similar manner as example 1 except that water was not supplied. The result is shown in table 1.

Reference Example 2

In the reference Example 1, a silver catalyst was prepared in a similar manner as the reference Example 1 except that 1 g of silver nitrate was used.

Example 4

The experiment was conducted in a similar manner as in Example 1 except that the silver catalyst obtained in the reference example 2 was used in place of the catalyst used in Example 1 and that reaction temperature was set at 180° C., and propylene oxide was obtained. Propylene conversion was 0.4%, and propylene oxide formation rate was 10 μmol/Hr.

Comparative Example 2

In example 4, the experiment was carried out in a similar manner as example 4 except that water was not supplied, and it was confirmed that propylene oxide was not generated. In addition, propylene conversion was 0.2%.

Reference Example 3

In the reference example 1, a silver catalyst was prepared in a similar manner as the reference example 1 except that mesoporous silicate prepared according to the method disclosed in Zeolite, 18, 408-416 (1997) was used in place of the crystalline silica having a framework structure isomorphous to that of ZSM-5.

Example 5

The experiment was carried out in a similar manner as example 1 except that silver catalyst obtained in the reference example 3 was used in place of the silver catalyst obtained in the reference example 1. Propylene conversion was 0.2%, and propylene oxide formation rate was 5% mol/Hr.

Comparative Example 3

In example 5, the experiment was carried out in a similar manner as example 5 except that water was not supplied, and it was confirmed that the propylene oxide was not formed. In addition, the propylene conversion was 0.1%.

Reference Example 4

To a solution containing 77 g of ion-exchange water, 60 g of ethanol, 7.3 g of n-dodecylamine and 6.7 g of silver nitrate charged in a flask was added dropwise a solution containing 44 g of ethanol and 30.4 g of tetraethylorthosilicate at 20-25° C. under stirring and was further stirred at the same temperature for 20 hours.

Precipitated solid material was collected by filtration and washed with 70 ml of ethanol thrice, and dried under reduced pressure at 70° C. The obtained powder was molded by tablet molding device, and sieved out with 24-48 mesh-screen and charged into a glass pipe and calcined under an air flow of 100 mL/minute, at 500° C. for 3 hours to prepare a silver catalyst.

Examples 6 to 7

2 ml of the silver catalyst prepared in the reference example 4 was charged into a fixed-bed glass tube reactor having an inner diameter of 10 mm and at atmospheric pressure, which corresponds to 0.1 MPa absolute, and at a reaction temperature of 200° C., propylene was fed at 360 mL/hr, air was fed at 360 mL/Hr, and water was fed as listed in Table 2 to the reactor to carry out the reaction. The results are shown in the following Table 2.

TABLE 2

|  | Example | | |
| --- | --- | --- | --- |
| Conditions | Ex. 6 | Ex. 7 | Comp. Ex. 4 |
| Water feed (mL/Hr) | 1 | 0.3 | 0 |
| Conv. of Propylene (%) | 2.4 | 1.6 | 0.7 |
| Propylene oxide (μmol/Hr) | 39 | 14 | 0 |

Comparative Example 4

In example 6, the experiment was carried out same as example 6 except that water was not supplied. The result is shown in Table 2.

Reference Example 5

3 g of silver carbonate and 10 g of ion-exchange water were charged into a flask and at 20-25° C. under stirring 4 g of aqueous 28 wt % ammonia was added thereto and was further stirred for 10 minutes. 2 g of oxalic acid, and 7.2 g of calcium carbonate were added thereto and stirred for 1 hour at the temperature.

The resulting mixture was dried at 70° C. and the obtained powder was molded by tablet molding device, and sieved out with 24-48 mesh-screen and charged into a glass pipe and calcined under an air flow of 100 mL/minute at 350° C. for 3 hours to prepare a silver catalyst.

Examples 8 to 9

2 ml of the silver catalyst prepared in the reference example 5 was charged into a fixed-bed glass tube reactor having an inner diameter of 10 mm and at atmospheric pressure, which corresponds to 0.1 MPa absolute, and at a reaction temperature of 200° C., propylene was fed at 360 mL/hr, air was fed at 360 mL/Hr, and water was fed as listed in Table 3 to the reactor to carry out the reaction. The results are shown in the following Table 3.

TABLE 3

| | Example | | |
|---|---|---|---|
| Conditions | Ex. 8 | Ex. 9 | Comparative Ex. 5 |
| Water feed (mL/Hr) | 0.3 | 1 | 0 |
| Conv. of Propylene (%) | 3.8 | 4.9 | 0.6 |
| Propylene oxide (µmol/Hr) | 92 | 110 | 12 |

Comparative Example 5

In example 8, the experiment was carried out same as example 8 except that water was not supplied. The results are shown in Table 3.

Reference Example 6

6.3 g of ethylenediamine, 1.9 g of ion-exchange water, 6.6 g of oxalic acid and 10.9 g of silver oxide (I) were charged into a flask at 20-25° C. under stirring and was further stirred for 1 hour. 2.2 g of ethanolamine, 9.2 g of calcium carbonate and 30 g of ion-exchange water were added thereto and stirred for 4 hours at the temperature. The resulting mixture was dried at 110° C. and the obtained powder was molded by tablet molding device, and sieved out with 24-48 mesh-screen and charged into a glass pipe and calcined under an air flow of 100 mL/minute at 350° C. for 3 hours to prepare a silver catalyst.

Examples 10-11

2 ml of the silver catalyst prepared in the Reference Example 6 was charged into a fixed-bed glass tube reactor having an inner diameter of 10 mm and at atmospheric pressure, which corresponds to 0.1 MPa absolute, and at a reaction temperature of 200° C., propylene was fed at 360 mL/hr, air was fed at 360 mL/Hr, and water was fed as listed in Table 4 to the reactor to carry out the reaction. The result was shown in the Table 4 below.

TABLE 4

| | Example | | |
|---|---|---|---|
| Conditions | Ex. 10 | Ex. 11 | Comparative Ex. 6 |
| Water feed (mL/Hr) | 0.3 | 1 | 0 |
| Conv. of Propylene (%) | 4.9 | 6.3 | 0.7 |
| Propylene oxide (µmol/Hr) | 100 | 107 | 14 |

Comparative Example 6

In example 10, the experiment was carried out in a similar manner as example 10 except that water was not supplied. The result is shown in Table 4 above.

Reference Example 7

At 20-25° C., 126 g of an aqueous silver nitrate solution containing 26 g of silver nitrate was added dropwise over 30 minutes to 657.7 g of a slurry containing 57.7 g of calcium carbonate and stirred for 2 hours. The resulting solid material was collected by filtration and washed four times with 100 ml of ion-exchange water to give 91 g of a mixture of silver carbonate/calcium carbonate. 9.1 g of the silver carbonate/calcium carbonate mixture was charged into a flask, and 10 g of ion-exchange water and 5.4 g of 26 wt % aqueous tetramethylammonium hydroxide were added thereto under stirring for 1 hour. The resulting mixture was dried under reduced pressure at 70° C. and then the obtained powder was molded by a tablet molding device and sieved out with 24 to 48 mesh-screen, and then charged into a glass pipe reactor and calcined at 350° C. for 3 hours under an air flow of 100 ml/min to prepare a silver catalyst.

Example 12

2 ml of the silver catalyst prepared in the Reference Example 7 was charged into a fixed-bed glass tube reactor having an inner diameter of 10 mm and at an atmospheric pressure, which corresponds to 0.1 MPa absolute, and at a reaction temperature of 200° C., propylene was fed at 360 mL/hr, air was fed at 360 mL/Hr, and water was fed as listed in Table 5 to the reactor to carry out the reaction. The result is shown in the following Table 5.

TABLE 5

| | Example | |
|---|---|---|
| Conditions | Ex. 12 | Comparative Ex. 7 |
| Water feed (mL/Hr) | 0.3 | 0 |
| Conv. of Propylene (%) | 4.9 | 3.6 |
| Propylene oxide (µmol/Hr) | 84 | 42 |

Comparative Example 7

In example 12, the experiment was carried out in a similar manner as example 12 except that water was not supplied. The result is shown in Table 5.

Reference Example 8

9.1 g of the silver carbonate/calcium carbonate mixture as prepared in the Reference Example 7, and 10 g of ion-exchange water were charged into a flask, and 2.1 g of ethylenediamine and 2.2 g of oxalic acid were added thereto at 20 to 25° C., and stirred for 1 hour.

The resulting mixture was dried at 100° C. and then the obtained powder was molded by tablet molding device and sieved out with 24 to 48 mesh-screen, and then charged into a glass pipe and calcined at 350° C. for 3 hours under an air flow of 100 ml/min to prepare a silver catalyst.

Examples 13-14

2 ml of the silver catalyst prepared in the Reference Example 8 was charged into a fixed-bed glass tube reactor having an inner diameter of 10 mm and at an atmospheric pressure, which corresponds to 0.1 MPa absolute, and at a reaction temperature of 200° C., propylene was fed at 360 mL/hr, air was fed at 360 mL/Hr, and water was fed as listed in Table 6 to the reactor to carry out the reaction. The result is shown in the following Table 6.

TABLE 6

| Conditions | Example | | Comparative |
| --- | --- | --- | --- |
|  | Ex. 13 | Ex. 14 | Ex. 8 |
| Water feed (mL/Hr) | 0.3 | 1 | 0 |
| Conv. of Propylene (%) | 3.6 | 4.5 | 0.4 |
| Propylene oxide ($\mu$mol/Hr) | 70 | 86 | 7 |

Comparative Example 8

In Example 13, the experiment was carried out same as Example 13 except that water was not supplied. The result is shown in Table 6.

Reference Example 9

9.1 g of the silver carbonate/calcium carbonate mixture as prepared in the Reference Example 7, and 10 g of ion-exchange water were charged into a flask, and 1.1 g of oxalic acid were added thereto at 20 to 25° C., and stirred for 1 hour. The resulting mixture was dried at 100° C. and then the obtained powder was molded by a tablet molding device and sieved out with 24 to 48 mesh-screen, and then charged into a glass pipe and calcined at 350° C. for 3 hours under an air flow of 100 ml/min to prepare the silver catalyst.

Examples 15-16

2 ml of the silver catalyst prepared in the Reference Example 9 was charged into a fixed-bed glass tube reactor having an inner diameter of 10 mm and at an atmospheric pressure, which corresponds to 0.1 MPa absolute, and at a reaction temperature of 200° C., propylene was fed at 360 mL/hr, and air was fed at 360 mL/Hr, and water was fed as listed in Table 7 to the reactor to carry out the reaction. The result is shown in the following Table 7.

TABLE 7

| Conditions | Example | | Comparative |
| --- | --- | --- | --- |
|  | Ex. 15 | Ex. 16 | Ex. 9 |
| Water feed (mL/Hr) | 0.3 | 1 | 0 |
| Conv. of Propylene (%) | 1.6 | 3.7 | 0.4 |
| Propylene oxide ($\mu$mol/Hr) | 30 | 54 | 12 |

Comparative Example 9

In Example 15, the experiment was carried out in a similar manner as Example 15 except that water was not supplied. The result is shown in Table 7.

Reference Examples 10 to 13

30 ml of ion-exchange water, silver carbonate in the amount as listed in Table 8, and 28% aqueous ammonium were added to a flask at a temperature range of 20° C. to 25° C. in said order. Then 5 g of calcium carbonate was added thereto to produce slurry, and a solution of mixture of hydrazine monohydrate in the amount as listed in Table 8 and 10 ml of water was added thereto over 10 minutes. After keeping the temperature for 1 hour, solid material was collected by filtration using filter paper. The solid material was washed with ion-exchange water and dried at 100° C. for 5 hrs to give the catalyst.

TABLE 8

| No. | $Ag_2CO_3$ (g) | 28% $NH_3$ (g) | $NH_2NH_2 \cdot H_2O$ (g) |
| --- | --- | --- | --- |
| Ref. Ex. 10 | 2.15 | 3.72 | 0.38 |
| Ref. Ex. 11 | 1.58 | 2.25 | 0.23 |
| Ref. Ex. 12 | 0.79 | 1.13 | 0.12 |
| Ref. Ex. 13 | 0.39 | 0.57 | 0.06 |

Examples 17 to 20

1 ml of the silver catalyst prepared in the Reference Examples 10 to 13 were each charged into a glass pipe reactor having an inner diameter of 10 mm and at an atmospheric pressure, which corresponds to 0.1 MPa absolute, and at a reaction temperature of 200° C., propylene was fed at 360 mL/hr, air was fed at 360 mL/Hr, and water was fed at 1 ml/Hr to the reactor to carry out the reaction. The results are shown in the following Table 9.

TABLE 9

| Conditions | Ex. 17 | Comp. Ex. 10 | Ex. 18 | Comp Ex. 11 | Ex. 19 | Comp. Ex. 12 | Ex. 20 | Comp. Ex. 13 |
|---|---|---|---|---|---|---|---|---|
| Catalyst (Ref. Ex. No.) | 10 | 10 | 11 | 11 | 12 | 12 | 13 | 13 |
| Conv. of Propylene (%) | 4.2 | 0.5 | 3.9 | 0.5 | 2.5 | 0.2 | 2.2 | 0.2 |
| Propylene oxide (μmol/Hr) | 59 | 8 | 75 | 10 | 28 | 3 | 28 | 2 |

Comparative Examples 10 to 13

Reactions were carried out in a similar manner as Examples 17 to 20 respectively except that water was not supplied in Examples 17 to 20. The results are shown in Table 9.

Reference Example 14 to 16

30 ml of ion-exchange water, silver carbonate in the amount as listed in Table 10, and 28% aqueous ammonium were added to a flask at a temperature range of 20° C. to 25° C. in said order. Then 5 g of calcium carbonate was added thereto to produce slurry, and a solution of aqueous 5% HCHO in the amount as listed in Table 10 was added thereto over 10 minutes. After keeping the resulting mixture at 100° C. for 3 hours and cooled to room temperature, resulting solid material was collected by filtration using filter paper. The solid material was washed with ion-exchange water and dried at 100° C. for 5 hours to give the catalyst.

TABLE 10

| No. | $Ag_2CO_3$ (g) | 28% $NH_3$ (g) | aq. 5% HCHO (g) |
|---|---|---|---|
| Ref. Ex. 14 | 2.15 | 3.72 | 27.6 |
| Ref. Ex. 15 | 1.58 | 2.25 | 16.7 |
| Ref. Ex. 16 | 0.79 | 1.13 | 8.4 |

Examples 21 to 23

1 ml of the silver catalyst prepared in the Reference Examples 14 to 16 were each charged into a fixed-bed glass tube reactor having an inner diameter of 10 mm and at an atmospheric pressure, which corresponds to 0.1 MPa absolute, and at a reaction temperature of 200° C., propylene was fed at 360 mL/hr, air was fed at 360 mL/Hr, and water was fed at 1 ml/Hr to the reactor to carry out the reaction. The results are shown in the following Table 11.

TABLE 11

| Conditions | Ex. 21 | Comp. Ex. 14 | Ex. 22 | Comp. Ex. 15 | Ex. 23 | Comp. Ex. 16 |
|---|---|---|---|---|---|---|
| Catalyst (Ref. Ex. No.) | 14 | 14 | 15 | 15 | 16 | 16 |
| Conv. of Propylene (%) | 2.4 | 0.2 | 3.5 | 0.3 | 2.9 | 0.2 |
| Propylene oxide (μmol/Hr) | 68 | 3 | 47 | 5 | 56 | 3 |

Comparative Examples 14 to 16

Reactions were carried out in a similar manner as Examples 21 to 23 respectively except that water was not supplied in Examples 21 to 23. The results are shown in Table 11.

Reference Examples 17 to 19

30 ml of ion-exchange water, silver carbonate in the amount as listed in Table 12, and 28% aqueous ammonium were added to a flask at a temperature range of 20° C. to 25° C. in said order. Then 5 g of calcium carbonate was added thereto to produce slurry, and ethanol in the amount as listed in Table 12 was added thereto. After keeping the resulting mixture at 100° C. for 3 hours and cooled to room temperature, the resulting solid material was collected by filtration using filter paper. The solid material was washed with ion-exchange water and dried at 100° C. for 5 hours to give the catalyst.

TABLE 12

| No. | $Ag_2CO_3$ (g) | 28% $NH_3$ (g) | Ethanol (g) |
|---|---|---|---|
| Ref. Ex. 17 | 2.15 | 3.72 | 30 |
| Ref. Ex. 18 | 1.58 | 2.25 | 30 |
| Ref. Ex. 19 | 0.79 | 1.13 | 30 |

Examples 24 to 26

1 ml of the silver catalyst prepared in the Reference Examples 17 to 19 were each charged into a fixed-bed glass tube reactor having an inner diameter of 10 mm and at an atmospheric pressure, which corresponds to 0.1 MPa absolute, and at a reaction temperature of 200° C., propylene was feed at 360 mL/hr, air was fed at 360 mL/Hr, and water was fed at 1 ml/Hr to the reactor to carry out the reaction. The results are shown in the following Table 13.

TABLE 13

| Conditions | Ex. 24 | Comp. Ex. 17 | Ex. 25 | Comp. Ex. 18 | Ex. 26 | Comp. Ex. 19 |
|---|---|---|---|---|---|---|
| Catalyst (Ref. Ex. No.) | 17 | 17 | 18 | 18 | 19 | 19 |
| Conv. of Propylene (%) | 3.1 | 0.1 | 4.0 | 0.2 | 2.6 | 0.1 |
| Propylene oxide (μmol/Hr) | 69 | 0 | 87 | 2 | 32 | 0 |

Comparative Examples 17 to 19

Reactions were carried out in a similar manner as Examples 24 to 26 respectively except that water was not supplied in Examples 24 to 26. The results are shown in Table 13.

The invention claimed is:

1. A process for producing propylene oxide, which comprises reacting propylene with oxygen in the presence of a silver catalyst and 0.2 mole or more of water per mol of propylene,
   wherein said water is added to the reaction, and
   wherein the silver catalyst is a silver-containing composition obtained by contacting
   i) a silver compound with a reducing agent in the presence of an alkaline earth or rare earth metal carbonate,
   ii) a silver metal or a silver compound or a mixture thereof, with an inorganic solid oxide, an acid, and a nitrogen-containing compound,
   iii) a silver metal or a silver compound or a mixture thereof with a metal carbonate, an acid, and a nitrogen-containing compound,
   iv) a silver compound with an inorganic solid oxide, a nitrogen-containing compound, and a reducing agent,
   v) a silver compound with a metal carbonate, and an acid,
   vi) a silver compound with a metal carbonate, and a nitrogen-containing compound, or
   vii) a calcined silver-containing composition obtained by calcining the composition of i) ii), iii), iv), v), or vi) above.

2. A process according to claim 1, wherein the inorganic solid oxide is a) silicon oxides, b) alumina, calcia, magnesia, titania or zirconia, or complex metal oxides thereof.

3. A process according to claim 1, wherein the reaction of propylene with oxygen in the presence of a silver catalyst and 0.2 mole or more of water per mol of propylene is conducted at a pressure range of 0.01 to 1 MPa absolute.

4. A process according to claim 1, wherein the amount of water is 0.2 mole to 20 moles per mol of the propylene.

5. A process according to claim 1, wherein the silver catalyst is a silver catalyst containing silver 1% to 70% by weight.

6. A process according to claim 2, wherein the silicon oxide is water-insoluble silicate or silica gel.

7. A process according to claim 6, wherein the water-insoluble silicate is zeolite or mesoporous silicate.

8. A process according to claim 1, wherein the metal carbonate is alkaline earth metal carbonate.

* * * * *